(12) United States Patent
First (10) Patent No.: US 8,871,224 B2
(45) Date of Patent: *Oct. 28, 2014

(54) BOTULINUM TOXIN THERAPY FOR SKIN DISORDERS

(75) Inventor: Eric First, Morristown, NJ (US)

(73) Assignee: Allergan, Inc., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/073,741

(22) Filed: Mar. 28, 2011

(65) Prior Publication Data

US 2011/0206731 A1    Aug. 25, 2011

Related U.S. Application Data

(63) Continuation-in-part of application No. 12/762,110, filed on Apr. 16, 2010, now Pat. No. 8,530,410, which is a continuation-in-part of application No. 10/731,973, filed on Dec. 9, 2003, now Pat. No. 8,048,423.

(51) Int. Cl.
| | |
|---|---|
| *A61K 39/08* | (2006.01) |
| *A61K 39/00* | (2006.01) |
| *A01N 37/18* | (2006.01) |
| *A61K 38/00* | (2006.01) |
| *A61P 31/04* | (2006.01) |
| *A61K 38/48* | (2006.01) |

(52) U.S. Cl.
CPC .................................. *A61K 38/4893* (2013.01)
USPC .................. 424/247.1; 424/239.1; 424/184.1; 514/2.4

(58) Field of Classification Search
None
See application file for complete search history.

(56) References Cited

U.S. PATENT DOCUMENTS

| | | | |
|---|---|---|---|
| 5,437,291 A | 8/1995 | Pasricha et al. | |
| 5,670,484 A | 9/1997 | Binder | 514/14 |
| 5,714,468 A | 2/1998 | Binder | 514/14 |
| 5,766,605 A | 6/1998 | Sanders et al. | 424/239.1 |
| 5,989,545 A | 11/1999 | Foster et al. | |
| 6,063,768 A | 5/2000 | First | |
| 6,139,845 A | 10/2000 | Donovan | |
| 6,299,893 B1 | 10/2001 | Schwartz et al. | 424/422 |
| 6,306,423 B1 | 10/2001 | Donovan et al. | |
| 6,312,708 B1 | 11/2001 | Donovan | |
| 6,423,319 B1 | 7/2002 | Brooks et al. | |
| 6,429,189 B1 | 8/2002 | Borodic | 514/2 |
| 6,447,787 B1 * | 9/2002 | Gassner et al. | 424/247.1 |
| 6,451,240 B1 | 9/2002 | Sherman et al. | 264/504 |
| 6,458,365 B1 | 10/2002 | Aoki et al. | |
| 6,464,986 B1 | 10/2002 | Aoki et al. | |
| 6,688,311 B2 | 2/2004 | Hanin | 128/898 |
| 6,896,886 B2 | 5/2005 | Aoki et al. | 424/184.1 |
| 7,149,574 B2 | 12/2006 | Yun et al. | 607/2 |
| 8,048,423 B2 | 11/2011 | First | |
| 2001/0036943 A1 | 11/2001 | Coe et al. | 514/220 |
| 2002/0028765 A1 | 3/2002 | Maurer | 514/2 |
| 2003/0036502 A1 | 2/2003 | Gassner et al. | 514/2 |
| 2003/0113349 A1 | 6/2003 | Coleman, III | 424/239.1 |
| 2003/0166004 A1 | 9/2003 | Gyuris et al. | 435/7.1 |
| 2003/0224019 A1 | 12/2003 | O'Brien | |
| 2003/0224020 A1 | 12/2003 | Zabudkin et al. | 424/239.1 |
| 2004/0060569 A1 | 4/2004 | Hanin | 128/898 |
| 2004/0087772 A1 | 5/2004 | Pastan et al. | 530/350 |
| 2004/0087893 A1 | 5/2004 | Kwon | 604/46 |
| 2004/0199103 A1 | 10/2004 | Kwon | 604/46 |
| 2004/0204471 A1 | 10/2004 | Seibert | 514/406 |
| 2004/0213815 A1 | 10/2004 | Ackerman | 424/239.1 |
| 2004/0220100 A1 | 11/2004 | Waugh et al. | 514/12 |
| 2005/0009910 A1 | 1/2005 | Hughes et al. | 514/559 |
| 2005/0031648 A1 | 2/2005 | Brin et al. | 424/239.1 |
| 2005/0058614 A1 | 3/2005 | Krauss | 424/70.1 |
| 2005/0059595 A1 | 3/2005 | Lasko et al. | 514/12 |
| 2005/0074466 A1 | 4/2005 | Suskind et al. | 424/247.1 |
| 2005/0123567 A1 | 6/2005 | First | 424/239.1 |
| 2005/0148935 A1 | 7/2005 | Dimitrova et al. | 604/116 |
| 2005/0175636 A1 | 8/2005 | Donovan | 424/239.1 |
| 2005/0175637 A1 | 8/2005 | Gassner et al. | 424/239.1 |
| 2005/0181977 A1 | 8/2005 | Hunter et al. | 514/2 |
| 2005/0196414 A1 | 9/2005 | Dake et al. | 424/239.1 |
| 2005/0208095 A1 | 9/2005 | Hunter et al. | 424/423 |
| 2005/0214325 A1 | 9/2005 | David | 424/239.1 |
| 2005/0214328 A1 | 9/2005 | Zeldis et al. | 424/239.1 |
| 2005/0220734 A1 | 10/2005 | First | 424/62 |
| 2005/0220820 A1 | 10/2005 | Sanders et al. | 424/239.1 |
| 2005/0239705 A1 | 10/2005 | Dake et al. | 514/12 |
| 2005/0260231 A1 | 11/2005 | Brin et al. | 424/239.1 |
| 2005/0261632 A1 | 11/2005 | Xu | 604/173 |
| 2006/0039930 A2 | 2/2006 | Gassner et al. | 424/239.1 |
| 2006/0057088 A1 | 3/2006 | Tankovich | 424/70.1 |
| 2006/0147492 A1 * | 7/2006 | Hunter et al. | 424/426 |
| 2006/0153876 A1 * | 7/2006 | Sanders | 424/239.1 |
| 2006/0165657 A1 | 7/2006 | Bernasconi et al. | 424/93.2 |
| 2007/0190043 A1 | 8/2007 | Sych et al. | 424/130.1 |
| 2008/0014159 A1 | 1/2008 | First | 424/62 |
| 2008/0044439 A1 | 2/2008 | David | 424/239.1 |
| 2010/0204126 A1 * | 8/2010 | Turkel et al. | 514/12 |
| 2011/0054442 A1 * | 3/2011 | Sanders | 604/506 |

OTHER PUBLICATIONS

U.S. Appl. No. 10/194,805, filed Jul. 11, 2002, Donovan, Stephen.
U.S. Appl. No. 10/731,973, filed Dec. 7, 2003, First, Eric F.

* cited by examiner

*Primary Examiner* — Gary Nickol
*Assistant Examiner* — Lakia Tongue
(74) *Attorney, Agent, or Firm* — Brigitte C. Phan; Ted Chan; Debra Condino (57) ABSTRACT

Methods for treating skin disorders by local administration of a Clostridial toxin, such as a botulinum toxin, to a patient with a skin disorder.

17 Claims, 1 Drawing Sheet

BOTULINUM TOXIN THERAPY FOR SKIN DISORDERS

CROSS REFERENCE TO RELATED APPLICATIONS

This application is a continuation in part of U.S. application Ser. No. 10/731,973, filed Dec. 9, 2003, and U.S. application Ser. No. 12/762,110, filed Apr. 16, 2010, both incorporated entirely by reference.

FIELD OF THE INVENTION

The present invention relates to methods for treating melanin related afflictions. In particular the present invention relates to methods for treating melanin related afflictions in humans by administration of a botulinum neurotoxin.

BACKGROUND

The skin is a protective membrane which covers the body and is composed of several layers including the epidermis and cornium. Melanocytes are specialized cells present in the skin which make and distribute the pigment melanin to surrounding keratinocytes, another type of skin cell. The color of the skin, hair and iris of the eyes is determined primarily by the presence or absence of melanin. The amount of melanin present can depend upon one's race as well as amount of exposure to sunlight. Exposure to sunlight increases melanin production as a protective mechanism (the tanning response) against the ultraviolet radiation found in sunlight. Hormones, such as melanocyte stimulating hormone are also known to affect melanin production.

The skin contains an extensive neural network of cholinergic and adrenergic nerves, including myelinated and unmyelinated afferent (sensory) and efferent fibers. It is known that melanocyte metabolism, including melanin production, (i.e. hair color and skin color) is regulated at least in part by various neuropeptides released by dermal nerves as well as by hormonal influences. Additionally, cutaneous nerve fibers released neuropeptides can also modify the activities of dermal immune cells. The close anatomical and physiological linkage between immune cells in the skin and cutaneous nerves forms the neuro-immuno-cutaneous system (NICS). Ultraviolet radiation can affect the activities of the NICS, including melanin synthesis and immunosuppression.

Furthermore, stress can affect hair growth and hair pigmentation. Thus, cutaneous nerves can influence hair follicle development, growth and/or cycling through release of various neurotransmitters, neuropeptides and neurotrophins. As a prominent source of neurotrophins, the hair follicle itself can influence its own innervation.

Skin and hair pigment disorders (melanin related afflictions) include melasma, pigment loss after skin damage, vitiligo, freckles and moles (nevi). Noncancerous skin pigment disorders include dermatofibromas, dermoid cyst, freckles, keloids, keratoacanthomas, lipomasmoles (nevi), atypical moles (dysplastic nevi), pyogenic granulomas, seborrheic keratoses, actinic keratosis, skin tags, pigment disorders: albinism, melasma, pigment loss after skin damage and vitiligo. Melanin disregulation related skin cancers include melanoma, basal cell carcinoma and squamous cell carcinoma.

Botulinum Toxin

The genus *Clostridium* has more than one hundred and twenty seven species, grouped according to their morphology and functions. The anaerobic, gram positive bacterium *Clostridium botulinum* produces a potent polypeptide neurotoxin, botulinum toxin, which causes a neuroparalytic illness in humans and animals referred to as botulism. The spores of *Clostridium botulinum* are found in soil and can grow in improperly sterilized and sealed food containers of home based canneries, which are the cause of many of the cases of botulism. The effects of botulism typically appear 18 to 36 hours after eating the foodstuffs infected with a *Clostridium botulinum* culture or spores. The botulinum toxin can apparently pass unattenuated through the lining of the gut and shows a high affinity for cholinergic motor neurons. Symptoms of botulinum toxin intoxication can progress from difficulty walking, swallowing and speaking to paralysis of the respiratory muscles and death.

Botulinum toxin type A is the most lethal natural biological agent known to man. About 50 picograms of a commercially available botulinum toxin type A (purified neurotoxin complex).sup.1 is a LD50 in mice (i.e. 1 unit). One unit of BOTOX® contains about 50 picograms (about 56 attomoles) of botulinum toxin type A complex. Interestingly, on a molar basis, botulinum toxin type A is about 1.8 billion times more lethal than diphtheria, about 600 million times more lethal than sodium cyanide, about 30 million times more lethal than cobra toxin and about 12 million times more lethal than cholera. Singh, Critical Aspects of Bacterial Protein Toxins, pages 63-84 (chapter 4) of Natural Toxins II, edited by B. R. Singh et al., Plenum Press, New York (1976) (where the stated LD50 of botulinum toxin type A of 0.3 ng equals 1 U is corrected for the fact that about 0.05 ng of BOTOX® equals 1 unit). One unit (U) of botulinum toxin is defined as the LD50 upon intraperitoneal injection into female Swiss Webster mice weighing 18 to 20 grams each. .sup.1 Available from Allergan, Inc., of Irvine, Calif. under the tradename BOTOX® in 100 unit vials)

Seven generally immunologically distinct botulinum neurotoxins have been characterized, these being respectively botulinum neurotoxin serotypes A, B, C.sub.1, D, E, F and G each of which is distinguished by neutralization with type-specific antibodies. The different serotypes of botulinum toxin vary in the animal species that they affect and in the severity and duration of the paralysis they evoke. For example, it has been determined that botulinum toxin type A is 500 times more potent, as measured by the rate of paralysis produced in the rat, than is botulinum toxin type B. Additionally, botulinum toxin type B has been determined to be non-toxic in primates at a dose of 480 U/kg which is about 12 times the primate LD50 for botulinum toxin type A. Moyer E et al., Botulinum Toxin Type B: Experimental and Clinical Experience, being chapter 6, pages 71-85 of "Therapy With Botulinum Toxin," edited by Jankovic, J. et al. (1994), Marcel Dekker, Inc. Botulinum toxin apparently binds with high affinity to cholinergic motor neurons, is translocated into the neuron and blocks the release of acetylcholine. Additional uptake can take place through low affinity receptors, as well as by phagocytosis and pinocytosis.

Regardless of serotype, the molecular mechanism of toxin intoxication appears to be similar and to involve at least three steps or stages. In the first step of the process, the toxin binds to the presynaptic membrane of the target neuron through a specific interaction between the heavy chain (the H chain or HC), and a cell surface receptor. The receptor is thought to be different for each type of botulinum toxin and for tetanus toxin. The carboxyl end segment of the HC appears to be important for targeting of the botulinum toxin to the cell surface.

In the second step, the botulinum toxin crosses the plasma membrane of the target cell. The botulinum toxin is first engulfed by the cell through receptor-mediated endocytosis, and an endosome containing the botulinum toxin is formed. The toxin then escapes the endosome into the cytoplasm of the cell. This step is thought to be mediated by the amino end segment of the HC, the HN, which triggers a conformational change of the toxin in response to a pH of about 5.5 or lower. Endosomes are known to possess a proton pump which decreases intra-endosomal pH. The conformational shift exposes hydrophobic residues in the toxin, which permits the botulinum toxin to embed itself in the endosomal membrane. The botulinum toxin (or at least the light chain of the botulinum) then translocates through the endosomal membrane into the cytoplasm.

The last step of the mechanism of botulinum toxin activity appears to involve reduction of the disulfide bond joining the heavy chain, H chain, and the light chain, L chain. The entire toxic activity of botulinum and tetanus toxins is contained in the L chain of the holotoxin; the L chain is a zinc (Zn++) endopeptidase which selectively cleaves proteins essential for recognition and docking of neurotransmitter-containing vesicles with the cytoplasmic surface of the plasma membrane, and fusion of the vesicles with the plasma membrane. Tetanus neurotoxin, botulinum toxin types B, D, F, and G cause degradation of synaptobrevin (also called vesicle-associated membrane protein (VAMP)), a synaptosomal membrane protein. Most of the VAMP present at the cytoplasmic surface of the synaptic vesicle is removed as a result of any one of these cleavage events. Botulinum toxin serotype A and E cleave SNAP-25. Botulinum toxin serotype C1 was originally thought to cleave syntaxin, but was found to cleave syntaxin and SNAP-25. Each of the botulinum toxins specifically cleaves a different bond, except botulinum toxin type B (and tetanus toxin) which cleave the same bond. Each of these cleavages block the process of vesicle-membrane docking, thereby preventing exocytosis of vesicle content.

Botulinum toxins have been used in clinical settings for the treatment of neuromuscular disorders characterized by hyperactive skeletal muscles (i.e. motor disorders). In 1989 a botulinum toxin type A complex was approved by the U.S. Food and Drug Administration for the treatment of blepharospasm, strabismus and hemifacial spasm. Subsequently, a botulinum toxin type A was also approved by the FDA for the treatment of cervical dystonia and for the treatment of glabellar lines, and a botulinum toxin type B was approved for the treatment of cervical dystonia. Non-type A botulinum toxin serotypes apparently have a lower potency and/or a shorter duration of activity as compared to botulinum toxin type A. Clinical effects of peripheral intramuscular botulinum toxin type A are usually seen within one week of injection. The typical duration of symptomatic relief from a single intramuscular injection of botulinum toxin type A averages about three months, although significantly longer periods of therapeutic activity have been reported.

Although all the botulinum toxins serotypes apparently inhibit release of the neurotransmitter acetylcholine at the neuromuscular junction, they do so by affecting different neurosecretory proteins and/or cleaving these proteins at different sites. For example, botulinum types A and E both cleave the 25 kiloDalton (kD) synaptosomal associated protein (SNAP-25), but they target different amino acid sequences within this protein. Botulinum toxin types B, D, F and G act on vesicle-associated protein (VAMP, also called synaptobrevin), with each serotype cleaving the protein at a different site. Finally, botulinum toxin type C1 has been shown to cleave both syntaxin and SNAP-25. These differences in mechanism of action may affect the relative potency and/or duration of action of the various botulinum toxin serotypes. Apparently, a substrate for a botulinum toxin can be found in a variety of different cell types. See e.g. Biochem J 1; 339 (pt 1):159-65:1999, and Mov Disord, 10(3):376:1995 (pancreatic islet B cells contains at least SNAP-25 and synaptobrevin).

The molecular weight of the botulinum toxin protein molecule, for all seven of the known botulinum toxin serotypes, is about 150 kD. Interestingly, the botulinum toxins are released by Clostridial bacterium as complexes comprising the 150 kD botulinum toxin protein molecule along with associated non-toxin proteins. Thus, the botulinum toxin type A complex can be produced by Clostridial bacterium as 900 kD, 500 kD and 300 kD forms. Botulinum toxin types B and C1 is apparently produced as only a 700 kD or 500 kD complex. Botulinum toxin type D is produced as both 300 kD and 500 kD complexes. Finally, botulinum toxin types E and F are produced as only approximately 300 kD complexes. The complexes (i.e. molecular weight greater than about 150 kD) are believed to contain a non-toxin hemaglutinin proteins and a non-toxin and non-toxic nonhemaglutinin protein. These two non-toxin proteins (which along with the botulinum toxin molecule comprise the relevant neurotoxin complex) may act to provide stability against denaturation to the botulinum toxin molecule and protection against digestive acids when a botulinum toxin is ingested. Additionally, it is possible that the larger (greater than about 150 kD molecular weight) botulinum toxin complexes may result in a slower rate of diffusion of the botulinum toxin away from a site of intramuscular injection of a botulinum toxin complex.

In vitro studies have indicated that botulinum toxin inhibits potassium cation induced release of both acetylcholine and norepinephrine from primary cell cultures of brainstem tissue. Additionally, it has been reported that botulinum toxin inhibits the evoked release of both glycine and glutamate in primary cultures of spinal cord neurons and that in brain synaptosome preparations botulinum toxin inhibits the release of each of the neurotransmitters acetylcholine, dopamine, norepinephrine (Habermann E., et al., Tetanus Toxin and Botulinum A and C Neurotoxins Inhibit Noradrenaline Release From Cultured Mouse Brain, J Neurochem 51(2); 522-527:1988) CGRP, substance P and glutamate (Sanchez-Prieto, J., et al., Botulinum Toxin A Blocks Glutamate Exocytosis From Guinea Pig Cerebral Cortical Synaptosomes, Eur J. Biochem 165; 675-681:1897. Thus, when adequate concentrations are used, stimulus-evoked release of most neurotransmitters can be blocked by botulinum toxin. See e.g. Pearce, L. B., Pharmacologic Characterization of Botulinum Toxin For Basic Science and Medicine, Toxicon 35(9); 1373-1412 at 1393; Bigalke H., et al., Botulinum A Neurotoxin Inhibits Non-Cholinergic Synaptic Transmission in Mouse Spinal Cord Neurons in Culture, Brain Research 360; 318-324:1985; Habermann E., Inhibition by Tetanus and Botulinum A Toxin of the release of [3H]Noradrenaline and [3H]GABA From Rat Brain Homogenate, Experientia 44; 224-226:1988, Bigalke H., et al., Tetanus Toxin and Botulinum A Toxin Inhibit Release and Uptake of Various Transmitters, as Studied with Particulate Preparations From Rat Brain and Spinal Cord, Naunyn-Schmiedeberg's Arch Pharmacol 316; 244-251:1981, and; Jankovic J. et al., Therapy With Botulinum Toxin, Marcel Dekker, Inc., (1994), page 5.

Botulinum toxin type A can be obtained by establishing and growing cultures of *Clostridium botulinum* in a fermenter and then harvesting and purifying the fermented mixture in accordance with known procedures. All the botulinum toxin serotypes are initially synthesized as inactive single chain proteins which must be cleaved or nicked by proteases to become neuroactive. The bacterial strains that make botulinum toxin serotypes A and G possess endogenous proteases and serotypes A and G can therefore be recovered from bacterial cultures in predominantly their active form. In contrast, botulinum toxin serotypes C1, D and E are synthesized by nonproteolytic strains and are therefore typically unactivated when recovered from culture. Serotypes B and F are produced by both proteolytic and nonproteolytic strains and therefore can be recovered in either the active or inactive form. However, even the proteolytic strains that produce, for example, the botulinum toxin type B serotype only cleave a portion of the toxin produced. The exact proportion of nicked to unnicked molecules depends on the length of incubation and the temperature of the culture. Therefore, a certain percentage of any preparation of, for example, the botulinum toxin type B toxin is likely to be inactive, possibly accounting for the known significantly lower potency of botulinum toxin type B as compared to botulinum toxin type A. The presence of inactive botulinum toxin molecules in a clinical preparation will contribute to the overall protein load of the preparation, which has been linked to increased antigenicity, without contributing to its clinical efficacy. Additionally, it is known that botulinum toxin type B has, upon intramuscular injection, a shorter duration of activity and is also less potent than botulinum toxin type A at the same dose level.

High quality crystalline botulinum toxin type A can be produced from the Hall A strain of Clostridium botulinum with characteristics of .gtoreq.3.times.107 U/mg, an A260/A278 of less than 0.60 and a distinct pattern of banding on gel electrophoresis. The known Shantz process can be used to obtain crystalline botulinum toxin type A, as set forth in Shantz, E. J., et al, Properties and use of Botulinum toxin and Other Microbial Neurotoxins in Medicine, Microbiol Rev. 56; 80-99:1992. Generally, the botulinum toxin type A complex can be isolated and purified from an anaerobic fermentation by cultivating Clostridium botulinum type A in a suitable medium. The known process can also be used, upon separation out of the non-toxin proteins, to obtain pure botulinum toxins, such as for example: purified botulinum toxin type A with an approximately 150 kD molecular weight with a specific potency of 1-2.times.108 LD50 U/mg or greater; purified botulinum toxin type B with an approximately 156 kD molecular weight with a specific potency of 1-2.times.108 LD50 U/mg or greater, and; purified botulinum toxin type F with an approximately 155 kD molecular weight with a specific potency of 1-2.times.107 LD50 U/mg or greater.

Botulinum toxins and/or botulinum toxin complexes can be obtained from List Biological Laboratories, Inc., Campbell, Calif.; the Centre for Applied Microbiology and Research, Porton Down, U.K.; Wako (Osaka, Japan), Metabiologics (Madison, Wis.) as well as from Sigma Chemicals of St Louis, Mo. Pure botulinum toxin can also be used to prepare a pharmaceutical composition.

As with enzymes generally, the biological activities of the botulinum toxins (which are intracellular peptidases) is dependant, at least in part, upon their three dimensional conformation. Thus, botulinum toxin type A is detoxified by heat, various chemicals surface stretching and surface drying. Additionally, it is known that dilution of a botulinum toxin complex obtained by the known culturing, fermentation and purification to the much, much lower toxin concentrations used for pharmaceutical composition formulation results in rapid detoxification of the toxin unless a suitable stabilizing agent is present. Dilution of the toxin from milligram quantities to a solution containing nanograms per milliliter presents significant difficulties because of the rapid loss of specific toxicity upon such great dilution. Since the botulinum toxin may be used months or years after the toxin containing pharmaceutical composition is formulated, the toxin can be stabilized with a stabilizing agent such as albumin and gelatin.

A commercially available botulinum toxin containing pharmaceutical composition is sold under the trademark BOTOX® (available from Allergan, Inc., of Irvine, Calif.). BOTOX® consists of a purified botulinum toxin type A complex, albumin and sodium chloride packaged in sterile, vacuum-dried form. The botulinum toxin type A is made from a culture of the Hall strain of Clostridium botulinum grown in a medium containing N—Z amine and yeast extract. The botulinum toxin type A complex is purified from the culture solution by a series of acid precipitations to a crystalline complex consisting of the active high molecular weight toxin protein and an associated hemagglutinin protein. The crystalline complex is re-dissolved in a solution containing saline and albumin and sterile filtered (0.2 microns) prior to vacuum-drying. The vacuum-dried product is stored in a freezer at or below −5.degree. C. BOTOX® can be reconstituted with sterile, non-preserved saline prior to intramuscular injection. Each vial of BOTOX® contains about 100 units (U) of Clostridium botulinum toxin type A purified neurotoxin complex, 0.5 milligrams of human serum albumin and 0.9 milligrams of sodium chloride in a sterile, vacuum-dried form without a preservative.

To reconstitute vacuum-dried BOTOX®, sterile normal saline without a preservative; (0.9% Sodium Chloride Injection) is used by drawing up the proper amount of diluent in the appropriate size syringe. Since BOTOX® may be denatured by bubbling or similar violent agitation, the diluent is gently injected into the vial. For sterility reasons BOTOX® is preferably administered within four hours after the vial is removed from the freezer and reconstituted. During these four hours, reconstituted BOTOX® can be stored in a refrigerator at about 2.degree. C. to about 8.degree. C. Reconstituted, refrigerated BOTOX® has been reported to retain its potency for at least about two weeks. Neurology, 48:249-53:1997.

It has been reported that botulinum toxin type A has been used in clinical settings as follows:

(1) about 75-125 units of BOTOX® per intramuscular injection (multiple muscles) to treat cervical dystonia;

(2) 5-10 units of BOTOX® per intramuscular injection to treat glabellar lines (brow furrows) (5 units injected intramuscularly into the procerus muscle and 10 units injected intramuscularly into each corrugator supercilii muscle);

(3) about 30-80 units of BOTOX® to treat constipation by intrasphincter injection of the puborectalis muscle;

(4) about 1-5 units per muscle of intramuscularly injected BOTOX® to treat blepharospasm by injecting the lateral pre-tarsal orbicularis oculi muscle of the upper lid and the lateral pre-tarsal orbicularis oculi of the lower lid.

(5) to treat strabismus, extraocular muscles have been injected intramuscularly with between about 1-5 units of BOTOX®, the amount injected varying based upon both the size of the muscle to be injected and the extent of muscle paralysis desired (i.e. amount of diopter correction desired).

(6) to treat upper limb spasticity following stroke by intramuscular injections of BOTOX® into five different upper limb flexor muscles, as follows: (a) flexor digitorum profundus: 7.5 U to 30 U(b) flexor digitorum sublimus: 7.5 U to 30 U(c) flexor carpi ulnaris: 10 U to 40 U(d) flexor carpi radialis: 15 U to 60 U(e) biceps brachii: 50 U to 200 U. Each of the five indicated muscles has been injected at the same treatment session, so that the patient receives from 90 U to 360 U of upper limb flexor muscle BOTOX® by intramuscular injection at each treatment session.

(7) to treat migraine, pericranial injected (injected symmetrically into glabellar, frontalis and temporalis muscles) injection of 25 U of BOTOX® has showed significant benefit as a prophylactic treatment of migraine compared to vehicle as measured by decreased measures of migraine frequency, maximal severity, associated vomiting and acute medication use over the three month period following the 25 U injection.

It is known that botulinum toxin type A can have an efficacy for up to 12 months (European J. Neurology 6 (Supp 4): S111-S1150:1999), and in some circumstances for as long as 27 months, when used to treat glands, such as in the treatment of hyperhydrosis. See e.g. Bushara K., Botulinum toxin and rhinorrhea, Otolaryngol Head Neck Surg 1996; 114(3):507, and The Laryngoscope 109:1344-1346:1999. However, the usual duration of an intramuscular injection of BOTOX® is typically about 3 to 4 months.

The success of botulinum toxin type A to treat a variety of clinical conditions has led to interest in other botulinum toxin serotypes. Two commercially available botulinum type A preparations for use in humans are BOTOX® available from Allergan, Inc., of Irvine, Calif., and DYSPORT® available from Beaufour Ipsen, Porton Down, England. A Botulinum toxin type B preparation (MYOBLOC®) is available from Elan Pharmaceuticals of San Francisco, Calif.

In addition to having pharmacologic actions at the peripheral location, botulinum toxins may also have inhibitory effects in the central nervous system. Work by Weigand et al, Nauny-Schmiedeberg's Arch. Pharmacol. 1976; 292, 161-165, and Habermann, Nauny-Schmiedeberg's Arch. Pharmacol. 1974; 281, 47-56 showed that botulinum toxin is able to ascend to the spinal area by retrograde transport. As such, a botulinum toxin injected at a peripheral location, for example intramuscularly, may be retrograde transported to the spinal cord.

U.S. Pat. No. 5,989,545 discloses that a modified clostridial neurotoxin or fragment thereof, preferably a botulinum toxin, chemically conjugated or recombinantly fused to a particular targeting moiety can be used to treat pain by administration of the agent to the spinal cord.

It has been speculated that botulinum toxin may bind to the melanin pigment present in the iris of rabbit eyes. Ishikawa H et al., Presynaptic effects of botulinum toxin type A on the neuronally evoked response of albino and pigmented rabbit iris sphincter and dilator muscles, Jpn J Opthalmol 2000 Mar. 4; 44(2):106-109. There are contradictory reports regarding periocular depigmentation in patients receiving multiple botulinum toxin injections. Roehm Pamela C. et al., Prevalence of periocular depigmentation after repeated botulinum toxin a injections in African American patients, J Neuro-Opthalmol 1999; 19(1):7-9. See also Friedland S, et al., Porcelinizing discolorization of the periocular skin following botulinum a toxin injections. J. Neuro-Opthalmol 1996 March; 16(1):70-2.

A botulinum toxin has also been proposed for or has been used to treat various skin disorders including warts, corns, calluses and bunions (U.S. patent application Ser. No. 10/731, 973), skin wounds (U.S. Pat. No. 6,447,787), various autonomic nerve dysfunctions (U.S. Pat. No. 5,766,605), tension headache, (U.S. Pat. No. 6,458,365), migraine headache pain (U.S. Pat. No. 5,714,468), post-operative pain and visceral pain (U.S. Pat. No. 6,464,986), hair growth and hair retention (U.S. Pat. No. 6,299,893 and GB 2,368,281)), psoriasis and dermatitis (U.S. Pat. No. 5,670,484), injured muscles (U.S. Pat. No. 6,423,319) various cancers (U.S. Pat. No. 6,139,845 and WO 02/09743), smooth muscle disorders (U.S. Pat. No. 5,437,291), nerve entrapment syndromes (U.S. patent application 2003 0224019), acne (WO 03/011333) and neurogenic inflammation (U.S. Pat. No. 6,063,768). Controlled release toxin implants are known (see e.g. U.S. Pat. Nos. 6,306,423 and 6,312,708) as is transdermal botulinum toxin administration (U.S. patent application Ser. No. 10/194,805).

It is known that a botulinum toxin can be used to: weaken the chewing or biting muscle of the mouth so that self inflicted wounds and resulting ulcers can heal (Payne M., et al, Botulinum toxin as a novel treatment for self mutilation in Lesch-Nyhan syndrome, Ann Neurol 2002 September; 52(3 Supp 1):S157); permit healing of benign cystic lesions or tumors (Blugerman G., et al., Multiple eccrine hidrocystomas: A new therapeutic option with botulinum toxin, Dermatol Surg 2003 May; 29(5):557-9); treat anal fissure (Jost W., Ten years' experience with botulinum toxin in anal fissure, Int J Colorectal Dis 2002 September; 17(5):298-302, and; treat certain types of atopic dermatitis (Heckmann M., et al., Botulinum toxin type A injection in the treatment of lichen simplex: An open pilot study, J Am Acad Dermatol 2002 April; 46(4):617-9).

Additionally, a botulinum toxin may have an effect to reduce induced inflammatory pain in a rat formalin model. Aoki K., et al, Mechanisms of the antinociceptive effect of subcutaneous Botox: Inhibition of peripheral and central nociceptive processing, Cephalalgia 2003 September; 23(7): 649. Furthermore, it has been reported that botulinum toxin nerve blockage can cause a reduction of epidermal thickness. Li Y, et al., Sensory and motor denervation influences epidermal thickness in rat foot glabrous skin, Exp Neurol 1997; 147:452-462 (see page 459). Finally, it is known to administer a botulinum toxin to the foot to treat excessive foot sweating (Katsambas A., et al., Cutaneous diseases of the foot: Unapproved treatments, Clin Dermatol 2002 November-December; 20(6):689-699; Sevim, S., et al., Botulinum toxin-A therapy for palmar and plantar hyperhidrosis, Acta Neurol Belg 2002 December; 102(4):167-70), spastic toes (Suputtitada, A., Local botulinum toxin type A injections in the treatment of spastic toes, Am J Phys Med Rehabil 2002 October; 81(10):770-5), idiopathic toe walking (Tacks, L., et al., Idiopathic toe walking: Treatment with botulinum toxin A injection, Dev Med Child Neurol 2002; 44 (Suppl 91):6), and foot dystonia (Rogers J., et al., Injections of botulinum toxin A in foot dystonia, Neurology 1993 April; 43(4 Suppl 2)).

Tetanus toxin, as wells as derivatives (i.e. with a non-native targeting moiety), fragments, hybrids and chimeras thereof can also have therapeutic utility. The tetanus toxin bears many similarities to the botulinum toxins. Thus, both the tetanus toxin and the botulinum toxins are polypeptides made by closely related species of *Clostridium* (*Clostridium tetani* and *Clostridium botulinum*, respectively). Additionally, both the tetanus toxin and the botulinum toxins are dichain proteins composed of a light chain (molecular weight about 50 kD) covalently bound by a single disulfide bond to a heavy chain (molecular weight about 100 kD). Hence, the molecular weight of tetanus toxin and of each of the seven botulinum toxins (non-complexed) is about 150 kD. Furthermore, for both the tetanus toxin and the botulinum toxins, the light chain bears the domain which exhibits intracellular biological (protease) activity, while the heavy chain comprises the receptor binding (immunogenic) and cell membrane translocational domains.

Further, both the tetanus toxin and the botulinum toxins exhibit a high, specific affinity for gangliocide receptors on the surface of presynaptic cholinergic neurons. Receptor mediated endocytosis of tetanus toxin by peripheral cholinergic neurons results in retrograde axonal transport, blocking of the release of inhibitory neurotransmitters from central synapses and a spastic paralysis. Contrarily, receptor mediated endocytosis of botulinum toxin by peripheral cholinergic neurons results in little if any retrograde transport, inhibition of acetylcholine exocytosis from the intoxicated peripheral motor neurons and a flaccid paralysis.

Finally, the tetanus toxin and the botulinum toxins resemble each other in both biosynthesis and molecular architecture. Thus, there is an overall 34% identity between the protein sequences of tetanus toxin and botulinum toxin type A, and a sequence identity as high as 62% for some functional domains. Binz T. et al., The Complete Sequence of Botulinum Neurotoxin Type A and Comparison with Other Clostridial Neurotoxins, J Biological Chemistry 265(16); 9153-9158: 1990.

Acetylcholine

Typically only a single type of small molecule neurotransmitter is released by each type of neuron in the mammalian nervous system, although there is evidence which suggests that several neuromodulators can be released by the same neuron. The neurotransmitter acetylcholine is secreted by neurons in many areas of the brain, but specifically by the large pyramidal cells of the motor cortex, by several different neurons in the basal ganglia, by the motor neurons that innervate the skeletal muscles, by the preganglionic neurons of the autonomic nervous system (both sympathetic and parasympathetic), by the bag 1 fibers of the muscle spindle fiber, by the postganglionic neurons of the parasympathetic nervous system, and by some of the postganglionic neurons of the sympathetic nervous system. Essentially, only the postganglionic sympathetic nerve fibers to the sweat glands, the piloerector muscles and a few blood vessels are cholinergic as most of the postganglionic neurons of the sympathetic nervous system secret the neurotransmitter norepinephine. In most instances acetylcholine has an excitatory effect. However, acetylcholine is known to have inhibitory effects at some of the peripheral parasympathetic nerve endings, such as inhibition of heart rate by the vagal nerve.

The efferent signals of the autonomic nervous system are transmitted to the body through either the sympathetic nervous system or the parasympathetic nervous system. The preganglionic neurons of the sympathetic nervous system extend from preganglionic sympathetic neuron cell bodies located in the intermediolateral horn of the spinal cord. The preganglionic sympathetic nerve fibers, extending from the cell body, synapse with postganglionic neurons located in either a paravertebral sympathetic ganglion or in a prevertebral ganglion. Since, the preganglionic neurons of both the sympathetic and parasympathetic nervous system are cholinergic, application of acetylcholine to the ganglia will excite both sympathetic and parasympathetic postganglionic neurons.

Acetylcholine activates two types of receptors, muscarinic and nicotinic receptors. The muscarinic receptors are found in all effector cells stimulated by the postganglionic, neurons of the parasympathetic nervous system as well as in those stimulated by the postganglionic cholinergic neurons of the sympathetic nervous system. The nicotinic receptors are found in the adrenal medulla, as well as within the autonomic ganglia, that is on the cell surface of the postganglionic neuron at the synapse between the preganglionic and postganglionic neurons of both the sympathetic and parasympathetic systems. Nicotinic receptors are also found in many nonautonomic nerve endings, for example in the membranes of skeletal muscle fibers at the neuromuscular junction.

Acetylcholine is released from cholinergic neurons when small, clear, is intracellular vesicles fuse with the presynaptic neuronal cell membrane. A wide variety of non-neuronal secretory cells, such as, adrenal medulla (as well as the PC12 cell line) and pancreatic islet cells release catecholamines and parathyroid hormone, respectively, from large dense-core vesicles. The PC12 cell line is a clone of rat pheochromocytoma cells extensively used as a tissue culture model for studies of sympathoadrenal development. Botulinum toxin inhibits the release of both types of compounds from both types of cells in vitro, permeabilized (as by electroporation) or by direct injection of the toxin into the denervated cell. Botulinum toxin is also known to block release of the neurotransmitter glutamate from cortical synaptosomes cell cultures.

A neuromuscular junction is formed in skeletal muscle by the proximity of axons to muscle cells. A signal transmitted through the nervous system results in an action potential at the terminal axon, with activation of ion channels and resulting release of the neurotransmitter acetylcholine from intraneuronal synaptic vesicles, for example at the motor endplate of the neuromuscular junction. The acetylcholine crosses the extracellular space to bind with acetylcholine receptor proteins on the surface of the muscle end plate. Once sufficient binding has occurred, an action potential of the muscle cell causes specific membrane ion channel changes, resulting in muscle cell contraction. The acetylcholine is then released from the muscle cells and metabolized by cholinesterases in the extracellular space. The metabolites are recycled back into the terminal axon for reprocessing into further acetylcholine.

What is needed therefore are therapeutically effective methods for treating melanin related afflictions.

SUMMARY

The present invention meets this need and provides methods for effectively treating a melanin related affliction by local administration of a Clostridial neurotoxin.

A method within the scope of the present invention for treating a melanin related affliction can have the step of local administration of a Clostridial neurotoxin to a location of a melanin related affliction of a patient. By local administration it is meant that the Clostridial neurotoxin is administered, as by injection, directly to, in, or to the vicinity of, a region of a melanin related affliction.

The Clostridial neurotoxin can be locally administered in an amount of between about $10^{-3}$ units/kg of patient weight and about 35 units/kg of patient weight. Preferably, the neurotoxin is locally administered in an amount of between about $10^{-2}$ U/kg and about 25 U/kg of patient weight. "U" is an abbreviation for "units." More preferably, the neurotoxin is administered in an amount of between about $10^{-1}$ U/kg and about 15 U/kg. In a particularly preferred method within the scope of the present invention, the neurotoxin is locally administered in an amount of between about 1 U/kg and about 10 U/kg. In a clinical setting it can be advantageous to inject from 1 U to 3000 U of a neurotoxin, such as botulinum toxin type A or B, to a melanin related affliction location by topical application or by subdermal administration, to effectively treat a melanin related affliction.

The present invention excludes any periocular use of a botulinum toxin to treat a melanin related affliction because: (1) the eyes are very sensitive to and can be deleteriously affected or permanently damaged by application to ocular tissue of an active agent (i.e. a pharmaceutical formulation); (2) there is no melanin pigment to be affected in or on the eye except for iris pigmentation and the present invention has no application to iris color change therapies, as such a therapy carries a high risk (i.e. upon accessing the iris) of damaging the friable iris; (3) to prevent inadvertent globe penetration or ocular damage upon administration of a pharmaceutical to the eye, and; (4) to prevent ptosis (excessive weakening or paralysis of one or more ocular muscles) and other undesired ocular effects from periocular administration of a Clostridial toxin, such as a botulinum neurotoxin.

A method according to my invention can be carried out by administration of a Clostridial toxin to a patient with, or who is predisposed to, a melanin related affliction. The Clostridial toxin used is preferably a botulinum toxin (as either a complex or as a pure botulinum toxin [i.e. about 150 kDa molecule, shorn of the attendant complex molecules], such as a botulinum toxin A, B, C, D, E, F or G. Administration of the Clostridial toxin can be by a transdermal route (i.e. by application of a Clostridial toxin in a cream, suspension, gel, emulsion, imbedded in a patch applied to the skin or in a lotion as vehicle), subdermal route (i.e. subcutaneous or intramuscular) or intradermal route of administration.

The dose of a Clostridial toxin used according to the present invention is less than the amount of toxin that would be used to paralyze or even to excessively weaken a muscle, since the intent of a method according to the present invention is not to paralyze or to excessively weaken a muscle but to treat a melanin related affliction.

The following definitions apply herein:

"About" means approximately or nearly and in the context of a numerical value or range set forth herein means.+−.10% of the numerical value or range recited or claimed.

"Affliction" includes a disease, disorder, problem and/or a cosmetically undesirable state or condition in an individual. "Melanin related affliction" means an affliction which is controlled or influenced by the present or absence of melanin. Thus, melanin related afflictions include various skin pigment disorders such as the noncancerous disorders dermatofibromas, dermoid cyst, freckles, keloids, keratoacanthomas, lipomasmoles (nevi), atypical moles (dysplastic nevi), pyogenic granulomas, seborrheic keratoses, actinic keratosis, and skin tags, as well as the pigment disorders albinism, melasma, pigment loss after skin damage and vitiligo, certain types of skin cancer such as melanoma, basal cell carcinoma, squamous cell carcinoma, and other related dysplastic diseases that involve disregulation of melanin. Melanin related afflictions also include desired skin and hair color pigmentation changes.

"Alleviating" means a reduction in the occurrence of a melanin related affliction symptom. Thus, alleviating includes some reduction, significant reduction, near total reduction, and total reduction of a melanin related affliction symptom. An alleviating effect may not appear clinically for between 1 to 7 days after administration of a Clostridial neurotoxin to a patient.

"Botulinum toxin" means a botulinum neurotoxin as either pure toxin (i.e. about 150 kDa weight molecule) or as a complex (i.e. about 300 to about 900 kDa weight complex comprising a neurotoxin molecule and one or more associated non-toxic molecules), and excludes botulinum toxins which are not neurotoxins such as the cytotoxic botulinum toxins C2 and C3, but includes recombinantly made, hybrid, modified, and chimeric botulinum toxins.

"Local administration" or "locally administering" means administration (i.e. by a subcutaneous, intramuscular, subdermal or transdermal route) of a pharmaceutical agent to or to the vicinity of a dermal or subdermal location of a patient.

"Treating" means to alleviate (or to eliminate) at least one symptom of a melanin related affliction, either temporarily or permanently.

The Clostridial neurotoxin is administered in a therapeutically effective amount to alleviate a symptom of a melanin related affliction. A suitable Clostridial neurotoxin may be a neurotoxin made by a bacterium, for example, the neurotoxin may be made from a *Clostridium botulinum, Clostridium butyricum*, or *Clostridium beratti*. In certain embodiments of the invention, the melanin related affliction can be treated by applying to (topical) or into (intra or transdermal) the skin of a patient a botulinum toxin. The botulinum toxin can be a botulinum toxin type A, type B, type C1, type D, type E, type F, or type G. The melanin related affliction alleviating effects of the botulinum toxin may persist for between about 2 weeks (i.e. upon administration of a short acting botulinum toxin, such as a botulinum toxin type E) and 5 years (i.e. upon implantation of a controlled release botulinum toxin implant). The botulinum neurotoxin can be a recombinantly made botulinum neurotoxins, such as botulinum toxins produced by an *E. coli* bacterium. In addition or alternatively, the botulinum neurotoxin can be a modified neurotoxin, that is a botulinum neurotoxin which has at least one of its amino acids deleted, modified or replaced, as compared to a native neurotoxin. The neurotoxin can be recombinantly made produced neurotoxin or a derivative or fragment of a recombinant made neurotoxin. A preferred botulinum toxin to use in the practice of the present invention is botulinum toxin type A.

A detailed embodiment of my invention can comprise a method for treating a melanin related affliction by local administration to a patient with a melanin related affliction of between about 1 unit and about 3,000 units of a botulinum toxin (for example between about 1-50 units of a botulinum toxin type A or between about 50 to 3,000 units of a botulinum toxin type B), thereby alleviating the melanin related affliction for between about two weeks and about 5 years.

My invention also encompasses a method for treating melanin related affliction by locally administering a botulinum toxin (such as a botulinum toxin type A, B, C, D, E, F or G, in an amount of from 1 unit to 3,000 units per treatment session) to a patient predisposed to experience melanin related affliction, thereby preventing the patient from experiencing a melanin related affliction. A patient predisposed to melanin related affliction is a human who has experienced melanin related affliction at least once within the last twelve months. The local administration can be carried out by subcutaneous or by topical administration of the botulinum toxin a location on or within the skin of the patient where a melanin related affliction is located. The melanin related affliction can be reduced in size by from about 20% to 100%.

DESCRIPTION OF EXEMPLARY EMBODIMENTS

The present invention is based upon the discovery that a melanin related affliction can be treated by local administration of a therapeutically effective amount of a Clostridial neurotoxin, such as a botulinum neurotoxin. The present invention is based upon the discovery that a botulinum toxin can be used to cause hair loss. The botulinum neurotoxin (such as a botulinum neurotoxin serotype A, B, C.sub.1 D, E, F or G) can be injected into or topically applied onto or in the vicinity of a melanin related affliction of a patient. Alternately, the botulinum toxin can be administered to an intradermal or subdermal neuron to thereby down regulate, inhibit or suppress a neuronally mediated or influenced melanin related affliction.

My invention includes a method for treating hair color changes and a liquid shampoo-based formulation that could be topically applied to the hair follicles. It is known that certain hormones which regulate hair color through affects upon melanin release are influenced by neuropeptides the release of which, as explained below, can be influenced by a botulinum toxin.

My invention also includes use of a botulinum toxin to treat skin pigment disorders (such as dermatofibromas, dermoid cyst, freckles, keloids, keratoacanthomas, lipomasmoles (nevi), atypical moles (dysplastic nevi), pyogenic granulomas, seborrheic keratoses, actinic keratosis, skin tags, albinism, melasma, pigment loss after skin damage and vitiligo, melanoma, basal cell carcinoma, squamous cell carcinoma, and other related dysplastic diseases that have disregulation of melanin) by applying an amount of a therapeutically effective dose of a botulinum toxin intradermally, subcutaneously, topically, via transdermal (patch, etc) in an effective amount to the affected pigmented regions.

Without wishing to be bound by theory a mechanism can be proposed for the efficasy of the present invention disclosed herein. Botulinum toxin has been shown in in vitro and in vivo models to inhibit release of various neuropeptides such as cGRP, substance P and the amino acid, glutamate and acetylcholine. (Durham, 2003; Cui et al., 2002; Welch et al., 2002). These neuropeptides act as modulators influencing melanin production and thereby skin pigmentation and hair color. Additionally, a botulinum toxin has been shown to have a direct effect on the skin (Li et al.). Thus, sensory and motor nerve denervation influence the epidermal thickness in rat foot glabrous skin, including denervation following a botulinum toxinA administration.

It is known that the skin contains an extensive neural network represented by cholinergic and adrenergic nerves and by myelinated and unmyelinated sensory fibers (Smolsky 2000)

BRIEF DESCRIPTION OF THE FIGURES

FIG. 1 sets forth a proposed mechanism for inhibition of melanin pigment production by a botulinum toxin. As shown by FIG. 1 neuropeptides released by sensory nerves that innervate the skin and contact epidermal and dermal cells can directly modulate functions of keratinocytes, Langerhans cells (LC), mast cells, dermal microvascular endothelial cells and infiltrating immune cells. Among these neuropeptides are the tachykinins, substance P (SP) and eurokinin A (NKA), calcitonin gene-related peptide (CGRP), vasoactive intestinal peptide (VIP) and somatostatin (SOM). As shown by FIG. 1 a botulinum toxin can inhibit release of cGRP, SP, and glutamate from sensory nerves, as well as SP release from hair follicle and can also inhibit direct release of these mediators from keratinocyte, and endothelial cells and melanocytes.

It is hypothesized that use of a botulinum toxin can inhibit release of acetylcholine and/or of another neurotransmitters or neuropeptides by one or more dermal nerves or structures which innervate or which influence a melanin related affliction, to thereby permit effective treatment of a melanin related affliction. Alternately, the administered Clostridial neurotoxin may have a direct effect upon the melanin related affliction. By effective treatment it is meant that the melanin related affliction becomes less painful, less inflammed and/or regresses (i.e. becomes smaller in size [i.e. thinner] or disappears altogether).

With regard to a proposed physiological mechanism for use of a Clostridial neurotoxin to treat a melanin related affliction as set forth herein, it is known that human keratinocytes can respond to acetylcholine. It is believed that acetylcholine is released by keratinocytes to function as a local hormone in the epidermis. Grando S. et al., Human keratinocytes synthesize, secrete, and degrade acetylcholine, J Invest Dermatol. 1993 July; 101(1):32-6. Human epidermal keratinocytes possess cholinergic enzymes, which synthesize and degrade acetylcholine, and express both nicotinic and muscarinic classes of cholinergic receptors on their cell surfaces. These epidermal keratinocyte cell surface receptors bind acetylcholine and initiate various cellular responses. Significantly, the presence in keratinocytes of a functional cholinergic system suggests a role for acetylcholine in most, if not all, aspects of keratinocyte function. Acetylcholine employs calcium as a mediator for its effects on keratinocytes. In turn, changes in calcium concentration can affect expression and function of keratinocyte cholinergic enzymes and cholinergic receptors. At different stages of their differentiation, keratinocytes demonstrate unique combinations of cholinergic enzymes and cholinergic receptor types. Grando S., Biological functions of keratinocyte cholinergic receptors, J Investig Dermatol Symp Proc. 1997 August; 2(1):41-8.

Importantly, skin innervation exerts influence on the proliferation of keratinocytes and the thickness of the epidermis. Huang et al., Influence of cutaneous nerves on keratinocyte proliferation and epidermal thickness in mice. Neuroscience. 1999; 94(3):965-73. Several lines of evidence suggest that nerves which terminate in the skin have profound influences on their target, the epidermis. See e.g. Grando S., Biological functions of keratinocyte cholinergic receptors, J Investig Dermatol Symp Proc. 1997 August; 2(1):41-8; Grando S., et al., Activation of keratinocyte nicotinic cholinergic receptors stimulates calcium influx and enhances cell differentiation. Invest Dermatol. 1996 September; 107(3):412-8; Ndoye A., et al., Identification and mapping of keratinocyte muscarinic acetylcholine receptor subtypes in human epidermis, J Invest Dermatol. 1998 September; 111(3):410-6; Palacios J., et al., Cholinergic neuropharmacology: an update, Acta Psychiatr Scand Suppl. 1991; 366:27-33; Whitehouse P., et al., Nicotinic and muscarinic cholinergic receptors in Alzheimer's disease and related disorders, J Neural Transm Suppl. 1987; 24:175-82; Arredondo J., et al., Central role of alpha7 nicotinic receptor in differentiation of the stratified squamous epithelium, J. Cell Biol. 2002 Oct. 28; 159(2):325-36; Andreadis S., et al., Keratinocyte growth factor induces hyperproliferation and delays differentiation in a skin equivalent model system, FASEB J. 2001 April; 15(6):898-906; Krnjevic K., Central cholinergic mechanisms and function. Prog Brain Res. 1993; 98:285-92; Epidermal expression of the full-length extracellular calcium-sensing receptor is required for normal keratinocyte differentiation, J Cell Physiol. 2002 July; 192(1):45-54; Grando S., et al., Human keratinocytes synthesize, secrete, and degrade acetylcholine J Invest Dermatol. 1993 July; 101(1):32-6; Zia S., et al., Receptor-mediated inhibition of keratinocyte migration by nicotine involves modulations of calcium influx and intracellular concentration, J Pharmacol Exp Ther. 2000 June; 293(3):973-81; Nguyen V., et al., Keratinocyte acetylcholine receptors regulate cell adhesion Life Sci. 2003 Mar. 28; 72(18-19):2081-5; Nguyen V., et al., Programmed cell death of keratinocytes culminates in apoptotic secretion of a humectant upon secretagogue action of acetylcholine J Cell Sci. 2001 March; 114 (Pt 6):1189-204; Grando S., et al., Keratinocyte muscarinic acetylcholine receptors: immunolocalization and partial characterization, J Invest Dermatol. 1995 January; 104(1):95-100; Lin Y., et al., (2001) Cutaneous nerve terminal degeneration in painful mononeuropathy, Experimental Neurology. 170(2):290-6; Pan C., et al., (2001) Degeneration of nociceptive nerve terminals in human peripheral neuropathy, Neuroreport. 12(4):787-92; Hsiung-F., et al., (2001) Quantitative pathology of cutaneous nerve terminal degeneration in the human skin, Acta Neuropathologica 102:455-461; Ko M., et al., Cutaneous nerve degeneration induced by acrylamide in mice, Neuroscience Letters. (2000) 293(3):195-8; Lin Y., et al., Quantitative sensory testing: normative values and its application in diabetic neuropathy, Acta Neurol Taiwan 1998; 7:176-184; T. Huang, et al., Influence of cutaneous nerves on keratinocyte proliferation and epidermal thickness in mice, Neuroscience 94:965-973, 1999; Hsieh S., et al., Pathology of nerve terminal degeneration in the skin, Journal of Neuropathology & Experimental Neurology. 2000; 59(4):297-307; Huang I. et al., Influence of cutaneous nerves on keratinocyte proliferation and epidermal thickness in mice, Neuroscience. 1999; 94(3):965-73; Hsieh S., et al., Modulation of keratinocyte proliferation by skin innervation. Journal of Investigative Dermatology, 1999; 113(4):579-86; Chen W., et al., Trophic interactions between sensory nerves and their targets, Journal of Biomedical Science. 1999; 6(2):79-85; Chiang H-Y, et al., Regional difference in epidermal thinning after skin denervation, Exp Neurol 1998; 154(1):137-45; Hsieh S., et al., Skin innervation and its influence on the epidermis, J Biomed Sci 1997; 4:264-268; Lee M., et al., Clinical and electrophysiological characteristics of inflammatory demyelinating neuropathies, Acta Neurol Taiwan 1997; 6:283-288; Wu T., et al., Demonstration of human papillomavirus (HPV) genomic amplification and viral-like particles from CaSki cell line in SCID mice, J Virol Methods 1997; 65:287-298; Hsieh S., et al., Epidermal denervation and its effects on keratinocytes and Langerhans cells, J Neurocytol 1996; 25:513-524; McCarthy B., et al., Cutaneous innervation in sensory neuropathies: evaluation by skin biopsy, Neurol 1995; 45:1848-1855; Griffin J., et al., Axonal degeneration and disorders of the axonal cytoskeleton. In: Waxman S., et al., The Axon. New York: Oxford University Press, 1995:375-390.

Thus, it can be postulated that a botulinum toxin can be used to induce denervation and thereby can treat a melanin related affliction—by preventing (i.e. downregulating) the release of various neuropeptides released by nerves which innervate the skin and affect melanin production. Among these neuropeptides are the tachykinins, substance P and neurokinin A, calcitonin gene-related peptide (CGRP), vasoactive intestinal peptide (VIP) and somatostatin, all of which have been reported to modulate skin cell functions such as cell proliferation. As set forth previously, release of most neurotransmitters and related neuropeptides can be blocked by botulinum toxin. See e.g. Hokfelt T., Neuropeptides in perspective: The last ten years, Neuron 1991; 7: 867-879; Xu Z-Q D et al, Galanin/GMAP- and NPY-like immunoreactivities in locus coeruleus and noradrenergic nerve terminals in the hippocampal formation and cortex with notes on the galanin-R1 and -R2 receptors, J. Comp. Neurol. 1998; 392: 227-252; Xu Z-Q D et al, Galanin-5-hydroxytryptamine interactions: Electrophysiological, immunohistochemical and in situ hybridization studies on rat dorsal raphe neurons with a note on galanin R1 and R2 receptors. Neuroscience 1998; 87: 79-94; Johnson M., Synaptic glutamate release by postnatal rat serotonergic neurons in microculture, Neuron 1994; 12: 433-442; Sneddon P., et al., Pharamcological evidence that adenosine triphosphate and noradrenaline are cotransmitters in the guinea-pig vas deferens. J. Physiol. 1984; 347: 561-580; Kaneko T., et al., Immunohistochemical demonstration of glutaminase in catecholaminergic and serotonergic neurons of rat brain, Brain Res. 1990; 507: 141-154; Kasakov L., et al., Direct evidence for concomitant release of noradrenaline, adenosine 5'-triphosphate and neuropeptide Y from sympathetic nerve supplying the guinea-pig vas deferens. J. Auton. Nerv. Syst. 1988; 22: 75-82; Nicholas A. et al., Glutamate-like immunoreactivity in medulla oblongata catecholamine/substance P neurons, Neuro Report 1990; 1: 235-238; Nicholas A. et al., Kupfermann I., Functional studies of cotransmission. Physiol. Rev. 1991; 71: 683-732.48: 545-59; Lundberg J., Pharmacology of cotransmission in the autonomic nervous system: Integrative aspects on amines, neuropeptides, adenosine triphosphate, amino acids and nitric oxide, Pharmacol. Rev. 1996; 48: 113-178; Hsieh S., et al., Skin Innervation and Its Effects on the Epidermis, J Biomed Sci. 1997; 4(5):264-268; Legat F., et al., Repeated subinflammatory ultraviolet B irradiation increases substance P and calcitonin gene-related peptide content and augments mustard oil-induced neurogenic inflammation in the skin of rats, Neurosci Lett. 2002 Sep. 6; 329(3):309-13; White S., et al., Asahina A., et al., Specific induction of cAMP in Langerhans cells by calcitonin gene-related peptide: relevance to functional effects, Proc Natl Acad Sci USA. 1995 Aug. 29; 92(18):8323-7; Inaba N., et al., Capsaicin-induced calcitonin gene-related peptide release from isolated rat stomach measured with a new chemiluminescent enzyme immunoassay, Jpn J. Pharmacol. 1996 November; 72(3):223-9; Hosoi J., et al., Regulation of Langerhans cell function by nerves containing calcitonin gene-related peptide, Nature. 1993 May 13; 363 (6425):159-63.

Figure 1:
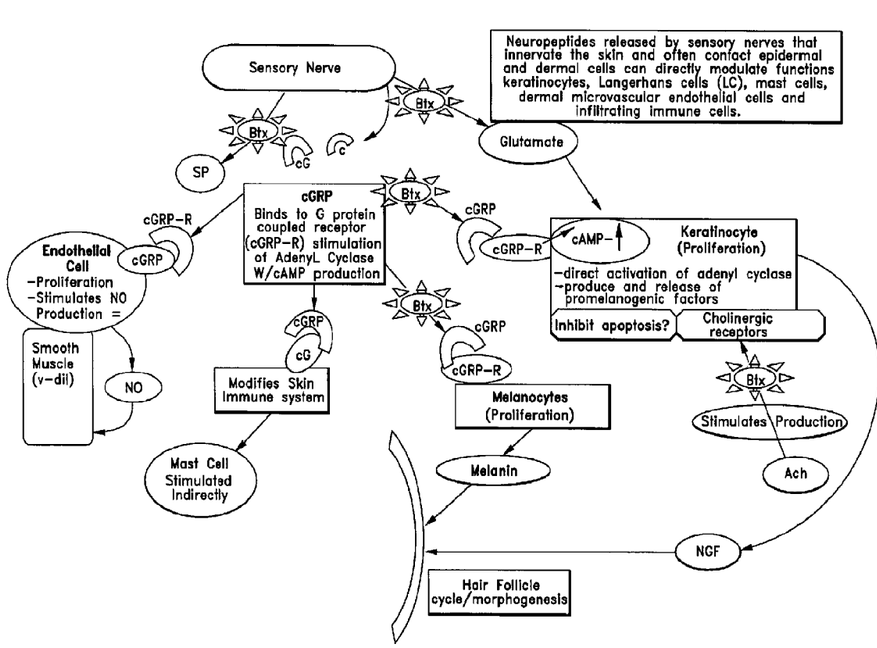

FIG. 1 illustrates mechanisms of action of a botulinum toxin ("a botulinum toxin" in FIG. 1). A botulinum toxin can inhibit release of cGRP, SP, and glutamate from dermal sensory nerves, and also inhibit direct release of these mediators from skin keratinocyte, endothelial and melanocyte cells. It is known that neuropeptides released by sensory nerves that innervate the skin and contact epidermal and dermal cells can directly modulate functions of keratinocytes, Langerhans cells (LC), mast cells, dermal microvascular endothelial cells and infiltrating immune cells. In FIG. 1 NO is nitrous oxide, cGRP is calcitonin gene-related peptide, Ach is acetylcholine, cGRP-R is the receptor for the cGRP molecule, v-dil means vasodilation and SP is substance P.

Furthermore, it has been demonstrated that denervation of the skin can cause the epidermis to began to degenerate or to become thinner. Hsieh S., et al., Modulation of keratinocyte proliferation by skin innervation, J Invest Dermatol. 1999 October; 113(4):579-86; Hsieh S., et al., Epidermal denervation and its effects on keratinocytes and Langerhans cells, J. Neurocytol. 1996 September; 25(9):513-24.); Chiang, et al., Regional difference in epidermal thinning after skin denervation, Exp Neurol 1998 November; 154(1):137-45; Li Y., et al., Sensory and motor denervation influence epidermal thickness in rat foot glabrous skin, Exp Neurol. 1997 October; 147(2):452-62 (botulinum toxin blockade caused epidermal thickness to be significantly reduced in the central area of the sole of the rat foot).

The amount of the Clostridial toxin administered according to a method within the scope of the disclosed invention can vary according to the particular characteristics of the melanin related affliction being treated, including its severity and other various patient variables including size, weight, age, and responsiveness to therapy. To guide the practitioner, typically, no less than about 1 unit and no more than about 50 units of a botulinum toxin type A (such as BOTOX®) is administered per injection site (i.e. to each melanin related affliction location injected), per patient treatment session. For a botulinum toxin type A such as DYSPORT®, no less than about 2 units and no more about 200 units of the botulinum toxin type A are administered per administration or injection site, per patient treatment session. For a botulinum toxin type B such as MYOBLOC®, no less than about 40 units and no more about 2500 units of the botulinum toxin type B are administered per administer or injection site, per patient treatment session. Less than about 1, 2 or 40 units (of BOTOX®, DYSPORT® and MYOBLOC® respectively) can fail to achieve a desired therapeutic effect, while more than about 50, 200 or 2500 units (of BOTOX®, DYSPORT® and MYOBLOC® respectively) can result in clinically observable and undesired muscle hypotonicity, weakness and/or paralysis.

More preferably: for BOTOX® no less than about 2 units and no more about 20 units of a botulinum toxin type A; for DYSPORT® no less than about 4 units and no more than about 100 units, and; for MYOBLOC®, no less than about 80 units and no more than about 1000 units are, respectively, administered per injection site, per patient treatment session.

Most preferably: for BOTOX® no less than about 5 units and no more about 15 units of a botulinum toxin type A; for DYSPORT® no less than about 20 units and no more than about 75 units, and; for MYOBLOC®, no less than about 200 units and no more than about 750 units are, respectively, administered per injection site, per patient treatment session. It is important to note that there can be multiple injection sites (i.e. a pattern of injections) for each patient treatment session.

Although examples of routes of administration and dosages are provided, the appropriate route of administration and dosage are generally determined on a case by case basis by the attending physician. Such determinations are routine to one of ordinary skill in the art (see for example, Harrison's Principles of Internal Medicine (1998), edited by Anthony Fauci et al., 14th edition, published by McGraw Hill). For example, the route and dosage for administration of a Clostridial neurotoxin according to the present disclosed invention can be selected based upon criteria such as the solubility characteristics of the neurotoxin chosen as well as the intensity and scope of a melanin related affliction.

The present invention is based on the discovery that local administration of a Clostridial toxin can provide significant and long lasting relief from a melanin related affliction. A Clostridial toxin used in accordance with the invention disclosed herein can inhibit transmission of chemical or electrical signals between select neuronal groups that are involved in generation of a melanin related affliction. The Clostridial toxins preferably are not cytotoxic to the cells that are exposed to the Clostridial toxin. The Clostridial toxin can inhibit neurotransmission by reducing or preventing exocytosis of neurotransmitter from the neurons exposed to the Clostridial toxin. Or the applied Clostridial toxin can reduce neurotransmission by inhibiting the generation of action potentials of the neurons exposed to the toxin. The melanin related affliction alleviation effect provided by the Clostridial toxin can persist for a relatively long period of time, for example, for more than two months, and potentially for several years.

Examples of Clostridial toxins within the scope of the present invention include neurotoxins made by *Clostridium botulinum, Clostridium butyricum* and *Clostridium beratti* species. In addition, the botulinum toxins used in the methods of the invention may be a botulinum toxin selected from a group of botulinum toxin types A, B, C, D, E, F, and G. In one embodiment of the invention, the botulinum neurotoxin administered to the patient is botulinum toxin type A. Botulinum toxin type A is desirable due to its high potency in humans, ready availability, and known use for the treatment of skeletal and smooth muscle disorders when locally administered by intramuscular injection. The present invention also includes the use of (a) Clostridial neurotoxins obtained or processed by bacterial culturing, toxin extraction, concentration, preservation, freeze drying, and/or reconstitution; and/or (b) modified or recombinant neurotoxins, that is neurotoxins that have had one or more amino acids or amino acid sequences deliberately deleted, modified or replaced by known chemical/biochemical amino acid modification procedures or by use of known host cell/recombinant vector recombinant technologies, as well as derivatives or fragments of neurotoxins so made. These neurotoxin variants retain the ability to inhibit neurotransmission between or among neurons, and some of these variants may provide increased durations of inhibitory effects as compared to native neurotoxins, or may provide enhanced binding specificity to the neurons exposed to the neurotoxins. These neurotoxin variants may be selected by screening the variants using conventional assays to identify neurotoxins that have the desired physiological effects of inhibiting neurotransmission.

Botulinum toxins for use according to the present invention can be stored in lyophilized, vacuum dried form in containers under vacuum pressure or as stable liquids. Prior to lyophilization the botulinum toxin can be combined with pharmaceutically acceptable excipients, stabilizers and/or carriers, such as albumin. The lyophilized material can be reconstituted with saline or water to create a solution or composition containing the botulinum toxin to be administered to the patient.

Although the composition may only contain a single type of neurotoxin, such as botulinum toxin type A, as the active ingredient to suppress neurotransmission, other therapeutic compositions may include two or more types of neurotoxins, which may provide enhanced therapeutic treatment of a melanin related affliction. For example, a composition administered to a patient may include botulinum toxin type A and botulinum toxin type B. Administering a single composition containing two different neurotoxins can permit the effective concentration of each of the neurotoxins to be lower than if a single neurotoxin is administered to the patient while still achieving the desired therapeutic effects. The composition administered to the patient may also contain other pharmaceutically active ingredients, such as, protein receptor or ion channel modulators, in combination with the neurotoxin or neurotoxins. These modulators may contribute to the reduction in neurotransmission between the various neurons. For example, a composition may contain gamma aminobutyric acid (GABA) type A receptor modulators that enhance the inhibitory effects mediated by the GABAA receptor. The GABAA receptor inhibits neuronal activity by effectively shunting current flow across the cell membrane. GABAA receptor modulators may enhance the inhibitory effects of the GABAA receptor and reduce electrical or chemical signal transmission from the neurons. Examples of GABAA receptor modulators include benzodiazepines, such as diazepam, oxaxepam, lorazepam, prazepam, alprazolam, halazeapam, chordiazepoxide, and chlorazepate. Compositions may also contain glutamate receptor modulators that decrease the excitatory effects mediated by glutamate receptors. Examples of glutamate receptor modulators include agents that inhibit current flux through AMPA, NMDA, and/or kainate types of glutamate receptors. The compositions may also include agents that modulate dopamine receptors, such as antipsychotics, norepinephrine receptors, and/or serotonin receptors. The compositions may also include agents that affect ion flux through voltage gated calcium channels, potassium channels, and/or sodium channels. Thus, the compositions used to treat a melanin related affliction can include one or more neurotoxins, such as botulinum toxins, in addition to ion channel receptor modulators that may reduce neurotransmission.

The neurotoxin may be administered by any suitable method as determined by the attending physician. The methods of administration permit the neurotoxin to be administered locally to a selected target tissue. Methods of administration include injection of a solution or composition containing the neurotoxin, as described above, and include implantation of a controlled release system that controllably releases the neurotoxin to the target tissue. Such controlled release systems reduce the need for repeat injections. Diffusion of biological activity of a botulinum toxin within a tissue appears to be a function of dose and can be graduated. Jankovic J., et al Therapy With Botulinum Toxin, Marcel Dekker, Inc., (1994), page 150. Thus, diffusion of botulinum toxin can be controlled to reduce potentially undesirable side effects that may affect the patient's cognitive abilities. For example, the neurotoxin can be administered so that the neurotoxin primarily effects neural systems believed to be involved in the generation of a melanin related affliction.

A polyanhydride polymer, GLIADEL® (Stolle R & D, Inc., Cincinnati, Ohio) a copolymer of poly-carboxyphenoxypropane and sebacic acid in a ratio of 20:80 has been used to make implants, and has been intracranially implanted to treat malignant gliomas. Polymer and BCNU can be co-dissolved in methylene chloride and spray-dried into microspheres. The microspheres can then be pressed into discs 1.4 cm in diameter and 1.0 mm thick by compression molding, packaged in aluminum foil pouches under nitrogen atmosphere and sterilized by 2.2 megaRads of gamma irradiation. The polymer permits release of carmustine over a 2-3 week period, although it can take more than a year for the polymer to be largely degraded. Brem, H., et al., Placebo-Controlled Trial of Safety and Efficacy of Intraoperative Controlled Delivery by Biodegradable Polymers of Chemotherapy for Recurrent Gliomas, Lancet 345; 1008-1012:1995.

Implants useful in practicing the methods disclosed herein may be prepared by mixing a desired amount of a stabilized neurotoxin (such as non-reconstituted BOTOX®) into a solution of a suitable polymer dissolved in methylene chloride. The solution may be prepared at room temperature. The solution can then be transferred to a Petri dish and the methylene chloride evaporated in a vacuum desiccator. Depending upon the implant size desired and hence the amount of incorporated neurotoxin, a suitable amount of the dried neurotoxin incorporating implant is compressed at about 8000 p.s.i. for 5 seconds or at 3000 p.s.i. for 17 seconds in a mold to form implant discs encapsulating the neurotoxin. See e.g. Fung L. K. et al., Pharmacokinetics of Interstitial Delivery of Carmustine 4-Hydroperoxycyclophosphamide and Paclitaxel From a Biodegradable Polymer Implant in the Monkey Brain, Cancer Research 58; 672-684:1998.

Local administration of a Clostridial toxin, such as a botulinum toxin, can provide a high, local therapeutic level of the toxin. A controlled release polymer capable of long term, local delivery of a Clostridial toxin to a target melanin related affliction location permits effective dosing of the target tissue. A suitable implant, as set forth in U.S. Pat. No. 6,306,423 entitled "Neurotoxin Implant", allows the direct introduction of a chemotherapeutic agent to a target tissue via a controlled release polymer. The implant polymers used are preferably hydrophobic so as to protect the polymer incorporated neurotoxin from water induced decomposition until the toxin is released into the target tissue environment.

Local administration of a botulinum toxin, according to the present invention, by injection or implant to a target tissue provides a superior alternative to systemic administration of pharmaceuticals to patients to alleviate a melanin related affliction.

The amount of a Clostridial toxin selected for local administration to a target tissue according to the present disclosed invention can be varied based upon criteria such as the severity of the melanin related affliction being treated, solubility characteristics of the neurotoxin toxin chosen as well as the age, sex, weight and health of the patient. For example, the extent of the area of skin influenced is believed to be proportional to the volume of neurotoxin injected, while the quantity of the melanin related affliction suppressant effect is, for most dose ranges, believed to be proportional to the concentration of a Clostridial toxin administered. Methods for determining the appropriate route of administration and dosage are generally determined on a case by case basis by the attending physician. Such determinations are routine to one of ordinary skill in the art (see for example, Harrison's Principles of Internal Medicine (1998), edited by Anthony Fauci et al., 14th edition, published by McGraw Hill).

Significantly, a method within the scope of the present invention can provide improved patient function. "Improved patient function" can be defined as an improvement measured by factors such as a reduced pain, reduced time spent in bed, increased ambulation, healthier attitude, more varied lifestyle and/or healing permitted by normal muscle tone. Improved patient function is synonymous with an improved quality of life (QOL). QOL can be assessed using, for example, the known SF-12 or SF-36 health survey scoring procedures. SF-36 assesses a patient's physical and mental health in the eight domains of physical functioning, role limitations due to physical problems, social functioning, bodily pain, general mental health, role limitations due to emotional problems, vitality, and general health perceptions. Scores obtained can be compared to published values available for various general and patient populations.

My invention also encompasses use of a botulinum toxin to cause hair removal. Stress has long been associated with disturbances in hair growth and hair pigmentation. A wide range of experimental data suggests that skin nerves can indeed modulate hair follicle (HF) development, growth and/or cycling via the release of neurotransmitters, neuropeptides and/or even of neurotrophins. It is therefore conceivable that stress-induced changes in the release of these agents from perifollicular sensory and autonomic nerve fibers can alter hair growth. Most classical mediators of systemic stress responses (e.g., substance p, ACTH, CRH, prolactin, catecholamines) are now also appreciated as hair growth modulators. Moreover, the HF itself is a potent source of these stress mediators, and expresses cognate receptors for many of them. Finally, mast cells, with their 'central switchboard' function in neurogenic inflammation, have recently surfaced as hair growth modulators. Stress mediators, as well as skin neuropeptides and neurotransmitters, can thus, impact hair growth indirectly via the modulation of mast cell activities. As a prominent source of neurotrophins, the hair follicle can influence its own innervation as well as neurotrophin-dependent mast cell functions. Reports of preliminary evidence that stress actually can inhibit hair growth in mice, demonstrates potential pathways by which stress may affect hair growth and color in the context of defined neuro-endocrine-immune circuits.

EXAMPLES

The following non-limiting examples provide those of ordinary skill in the art with specific preferred methods to treat conditions within the scope of the present invention and are not intended to limit the scope of the invention. In the following examples various modes of non-systemic administration of a Clostridial neurotoxin can be carried out. For example, by topical application (cream or transdermal patch), subcutaneous injection, or by implantation of a controlled release implant.

Example 1

Use of a Botulinum Toxin to Treat a Bone Spur

A 61 year old diabetic female presents with a pain that has developed at the bottom of her heel, and it has gotten worse. The patient is not aware of having had any injury that caused it. The patient is diagnosed with a painful bone spur at the center of the left heel. She reports a dull ache most of the time, but when the patient first gets out of the bed in the morning, or when getting up after sitting for a period of time during the day, the pain in the heel is almost unbearable, felling like the heel has been bruised, from falling on a rock barefoot, but it is worse. Several therapies including topical lidocaine, NSAIDS, and therapy are tried with little relief. Surgery is not an option due to the poor blood circulation of the patient's lower limbs. Therefore, botulinum toxin type A as 30 units total can be applied following use of a topical anesthetic, 10 U/site in three subcutaneous injection sites spaced evenly apart over the painful area. On follow-up 2 weeks later, the patient can report significant relief of pain and can tolerate walking. Four weeks later the patient can reported no pain and be able to tolerate walking greater distances than two weeks earlier.

Example 2

Use of a Botulinum Toxin to Treat Corns and Bunions

A 54 year old male who has been walking extensively at a large amusement park for three days with his grandchildren, reports significant pain on the proximal right side of his great toe, and on the plantar side of the foot pad on the same foot. The pain can become excruciating and dehabilitating. The patient has had a history of painful corns and bunions on both feet, which are recurrent, despite medical and orthotic treatment. Upon examination, a 6 $cm^2$ growth consistent with a corn and a 8 $cm^2$ circular, inflamed area on the plantar side, consistent with a bunion, is noted. A treatment with a botulinum toxin type A can be commenced as 50 U of toxin injected (2 sites/25 U each) intradermally into the corn and 30 U into the bunion. 14 days later, the patient can report significant relief in both affected areas. Two months later, the patient can report a reduction of over 50% in the size of the corn and 60% of the size of the bunion, with no pain. The patient can be able to return to normal walking activities and can also tolerate walking great distances.

Example 3

Use of a Botulinum Toxin to Treat Genital Warts

A 48 year old female presents with a history of genital warts. Examination of the patient reveals six flesh-colored bumps or tiny, cauliflower-like maculopapular warts of various sizes (0.05 $cm^2$ to 2 $cm^2$). The patient had been treated with several different treatment methods; direct application of bleomycin, acetylsilic acid, with little or no relief. The patient refuses laser or other types of invasive methods of treatments. A botulinum toxin type A is applied directly into the wart areas via intra-dermal injection, in an effective amount of, but not limited to 5 U/$cm^2$, for a total of 30 U. Upon follow up 4 weeks later, 3 of the smaller warts, can have disappeared completely and at 2 months, the patient can report disappearance of the remaining warts.

Example 4

Use of a Botulinum Toxin to Treat Plantar Warts

A 54 year old male has a history of painful plantar warts and returns to the clinic following an exacerbation of wart growth on the plantar region of his right foot. Upon examination, 3 various sized warts (1 $cm^2$, 2.5 $cm^2$ and 4.4 $cm^2$), with a rubor colored ring surrounding 2 of the 3 warts, suggesting inflammation. Patient has tried in bleomycin but relief was minimal and caused significant pain following injection. Therefore, a botulinum neurotoxin is considered as an alternative and 5 U/$cm^2$ can be applied in a topical formulation directly to the wart for a total of 45 U. On follow up 2 months later, the patient can report complete relief of pain and upon examination, there were no signs of inflammation (rubor rings not present), and 2 of the 3 warts had disappeared completely with only .about.1 $cm^2$ of the 4.4 $cm^2$ wart visible.

Example 5

Method for Treating Non-Cancerous Dermatofibromas

A thirty three year-old female patient presents with multiple pigmented, raised lesions on both her left and right calves which have remained relatively unchanged for the previous 10 years. Biopsy of several of the lesions can find benign dermatofibromas excised under local anesthesia. Post-operatively, small but noticeable scars can result from the procedure and histology can confirmed the clinical diagnosis of benign dermatofibromas. The lesions can reappear and the patient can be upset due to their unsightly appearance. Dermatofibromas are a relatively common cutaneous fibrohistiocytic tumor with a marked tendency to recur locally, and therefore, a non-invasive focal therapy is preferred. A clinician can recommend a course of intra-lesional injections of botulinum toxin type A. Ten dermatofibromas can be identified, ranging in size of 5-15 $cm^2$. Botulinum toxin type-A is reconstituted in 2 cc of sterile unpreserved saline and can be applied via intra-lesional injection (just below lesion surface) with 1 U/$cm^2$ surface area (i.e. 5-15 U/lesion times 10 lesions for a total of 150 U). Upon follow-up 6 weeks later, the patient and clinician can be pleased to report that 8 of the 10 lesions had markedly reduced in both size and in color; from a dark brown to light tan color. After a second application, this time with a topical preparation of botulinum toxin type A reconstituted with 1 cc of sterile unpreserved saline and admixed with a suitable emollient carrier at a ratio of 1 U/1 $cc^2$ and applied in a ratio of 1 cc/1 $cm^2$ the patient can report that all lesions have disappeared and no further evidence of dermatofibromas can be present.

Example 6

Method for Treating Skin Lesions

A 51 year old female can be seen in a clinic for 8-10 skin lesions on her face and neck region. Cryosurgical methods can fail to remove the lesions on her neck and cryosurgery carries the risk of scarring if repeated. Therefore, a course of botulinum toxin type A can be attempted. Ten units of a botulinum toxin type A can be injected intradermally into each of the 2-4 mm lesions. On follow up 4 weeks later, only 2 lesions can be noticeable, all others can have resolved. Three months later no can be no evidence of lesions.

Example 7

Method for Treating Nevi

A 48 year old male can be seen in the clinic for multiple nevi (moles) on his upper back and right shoulder. Six dark raised moles about 3-10 cm in diameter can be observed. 10-15 U of a botulinum toxin type A can be injected intradermally into the base of each nevi. Four weeks later the patient can report complete resolution of 2-3 cm nevi, and 3 other mid sized nevi as being very faint. Three months later patient can report complete resolution of the nevi.

Example 8

Method for Treating Melanoma

A 75-year-old woman can present with a one-year history of a pigmented, 5-mm lesion on the right posterior leg, and several pigmented lesions found on her right ear, face, and left arm. The lesion can have recently enlarged and darkened. Examination can show a nearly symmetrical homogenous, dark-brown, papule with a smooth border. Clinically, the first diagnosis can be melanocytic nevus. However, the lesion can appear different than the patient's other moles, and her history of recent onset and progressive increase in size with darkening of color can lead to a punch excision. Histopathologic investigation can show proliferation of atypical melanocytes forming irregular nests at the dermal-epidermal junction. Some melanocytes can be found at elevated levels within the epidermis. No invasive malignant melanoma may be present. The diagnosis of malignant melanoma in situ can be made, and prompt removal using a wide excision can be necessary. To ensure complete removal, it can be decided to first pre-treat the area with a course of botulinum toxin type A. 20 U of botulinum toxin type A can be reconstituted in 1 cc sterile unpreserved saline and injected into the center of the lesion. Two weeks later, the excision procedure can be performed and then followed two weeks post-operatively with an application of 100 U of botulinum toxin type B. Additionally, the patient's other non-melanocytic lesions on her right ear, face and on multiple nevi on her left arm can be treated via sub-cutaneous injection of a combination of botulinum toxin type A (0.5 U/cm.sup.2) and B (2.5 U/cm.sup.2). On follow-up six weeks later, 80% of the non-melanocytic nevi can be completely absent, and the melanocytic nevus can show no appearance of spreading or reformation.

Example 9

Method for Treating Freckles

A light skinned blond-haired male, 23 year-old immigrant worker can be seen in the clinic due to the excessive formation of numerous tanned macules (freckles) following extended exposure to summer sunlight, while working outdoors. Since the patient can insist on continuing to work in exposed sunlight and is concerned of potential skin damage and unsightly patchy appearance, he can decide to seek treatment. Upon examination, numerous macules can be found on the skin in the regions of the face and upper shoulder areas. A course of a botulinum toxin type A formulation as a topical formulation containing 150 units of the botulinum toxin admixed with a topical emollient containing a sunscreen of SPF 30 (1 U/1 cc) can be applied to the affected areas (1 cc/1 cm.sup.2). Upon follow up one month later, 70 percent of the maculae can be resolved, and the patient can continue application of sunscreen only and upon follow up at 3 months, 95% of the maculae can be resolved (i.e. can have disappeared).

Example 10

Method for Treating Albinism

A 12 year old male can present with a history of oculocutaneous albinism (OCA), a skin pigmentation disorder. Since this boy thrives on outdoor activities despite the effects of sunlight, a course of a hybrid formulation of the heavy chain-only (100 Kd) of botulinum toxin type-A and Ro31-8220, a potent inhibitor of protein kinase-C, admixed in a topical lotion formulation can be decided upon. A suitable amount (1 cc/1 cm.sup.2) of the formulation can be applied to cover the bodily areas most exposed to sunlight, including face, neck, shoulder region, arms and legs. The procedure can be repeated 2 months later, and following both visits the use of a sunscreen with an SPF of 30 can be reinforced. Upon follow-up, at 6 months, noticeable darkening of the treated areas can be observed. The patient can report increased tolerance to sun exposure and can report no sun burns. The patient can be retreated over the next 6 months where appropriate melanin skin production (adequate to prevent burning following 60 minutes of sun exposure) is noted. The same formulation can be used to treat a patient with pigment loss after skin damage.

Example 11

Method for Changing Hair Color

A 58 year-old single male can be concerned that the premature graying of his hair contributed to his ability to find a future wife, and can be seen in a dermatology clinic. Despite numerous attempts with several different hair coloring methods, the patient's hair may not change to darker color. A course of a hybrid formulation of containing heavy chains-only (100 Kd) of both botulinum toxin type-A and type-F and Ro31-8220, a potent inhibitor of protein kinase-C, admixed in a topical shampoo formulation can be decided upon. A suitable amount (1 cc/1 cm.sup.2) of the shampoo can be applied by the clinician using sterile protective gloves, along with a preventative barrier to restrict application to the patients scalp region. After two successive shampoo treatments with the same formulation spaced 4 weeks apart, a very noticeable change in hair color can be observed: from light gray to a medium black color.

Example 12

Method for Causing Hair Loss

A 21 year female college student can be seen in a clinic for hair removal. The patient can have undergone previous wax treatments and laser hair removal treatments but can be exquisitely sensitive and may not tolerate the associated pain. Therefore, a relatively non-invasive course of intra-dermal botulinum toxin type A can be decided upon. A total of 300 units of a Botulinum toxin type-A, reconstituted in sterile unpreserved saline in a concentration of 100 U/2 cc's, can be administered via intradermal application to both axillae (1

U/2 cm2) and to both legs. Upon follow up at 12 weeks a noticeable decrease in hair in both axillae and on the legs can be observed. The same procedure can be repeated and upon follow up 6 weeks later, no observable hair can be noted in either axillae or leg. At one year follow up following the last visit, hair growth can be beginning with minimal hair on the legs only In each of the examples above a botulinum toxin type B, C, D, E, F or G can be substituted for the botulinum toxin type A used above, for example by use of 250 units of a botulinum toxin type B. The specific amount of a botulinum toxin (such as BOTOX® administered depends upon a variety of factors to be weighed and considered within the discretion of the attending physician and in each of the examples 10 insignificant amounts of botulinum toxin enter appear systemically with no significant side effects.

A method for treating a skin disorder according to the invention disclosed herein has many benefits and advantages, including the following:

1. the symptoms of a skin disorder can be dramatically reduced or eliminated.
2. the symptoms of a skin disorder can be reduced or eliminated for at least about two weeks to about six months per injection of neurotoxin and for from about one year to about five years upon use of a controlled release neurotoxin implant.
3. the injected or implanted Clostridial neurotoxin shows little or no tendency to diffuse or to be transported away from the intramuscular (or intradermal or subdermal) injection or implantation site.
4. few or no significant undesirable side effects occur from intramuscular (or intradermal or subdermal) injection or implantation of the Clostridial neurotoxin.
5. the present methods can result in the desirable side effects of greater patient mobility, a more positive attitude, and an improved quality of life.

Although the present invention has been described in detail with regard to certain preferred methods, other embodiments, versions, and modifications within the scope of the present invention are possible. For example, a wide variety of neurotoxins can be effectively used in the methods of the present invention. Additionally, the present invention includes local administration methods to alleviate a skin disorder wherein two or more neurotoxins, such as two or more botulinum toxins, are administered concurrently or consecutively. For example, botulinum toxin type A can be administered until a loss of clinical response or neutralizing antibodies develop, followed by administration of botulinum toxin type B. Alternately, a combination of any two or more of the botulinum serotypes A-G can be locally administered to control the onset and duration of the desired therapeutic result. Furthermore, non-neurotoxin compounds can be administered prior to, concurrently with or subsequent to administration of the neurotoxin to proved adjunct effect such as enhanced or a more rapid onset of denervation before the neurotoxin, such as a botulinum toxin, begins to exert its therapeutic effect.

A botulinum toxin can be administered by itself or in combination of one or more of the other botulinum toxin serotypes. The botulinum toxin can be a recombinantly made or a hybrid botulinum toxin.

My invention also includes within its scope the use of a neurotoxin, such as a botulinum toxin, in the preparation of a medicament for the treatment of a skin disorder, by local administration of the neurotoxin.

All references, articles, patents, applications and publications set forth above are incorporated herein by reference in their entireties.

Accordingly, the spirit and scope of the following claims should not be limited to the descriptions of the preferred embodiments set forth above.

What is claimed is:

1. A method for treating a keloid in a patient in need thereof, the method comprising the step of administering a therapeutically effective amount of a botulinum toxin complex to the keloid, to thereby treat the keloid; wherein the therapeutically effective amount administered is less than an amount used to paralyze a muscle, ranging between about $10^{-3}$ units/kg of patient weight and about 35 units/kg of patient weight, and which reduces the keloid in size by from about 20% to 100%.

2. The method of claim 1, wherein the botulinum toxin is selected from the group consisting of botulinum toxin types A, B, C, D, E, F and G.

3. The method of claim 1, wherein the botulinum toxin is a botulinum toxin type A.

4. The method of claim 1, wherein the administration is by topical or subcutaneous administration of the botulinum toxin.

5. The method of claim 1, wherein administration of a botulinum toxin type A is no less than about 1 to about 200 units per patient treatment session.

6. The method of claim 2 wherein administration of a botulinum toxin type B is no less than about 40 to about 2500 units per patient treatment session.

7. A method for treating a symptom associated with a keloid in a patient in need thereof, the method comprising the step of administering a therapeutically effective amount of a botulinum toxin complex to the keloid, thereby treating the symptom associated with the keloid, wherein the therapeutically effective amount administered is less than an amount used to paralyze a muscle, ranging between about $10^{-3}$ units/kg of patient weight and about 35 units/kg of patient weight, and which reduces the keloid in size by from about 20% to 100%.

8. The method of claim 7, wherein the botulinum toxin is selected from the group consisting of botulinum toxin types A, B, C, D, E, F and G.

9. The method of claim 7, wherein the administration is by injection directly to the keloid.

10. The method of claim 7, wherein the symptom is selected from the group consisting of pain, inflammation and vascularization.

11. The method of claim 7, wherein administration is transdermal or subdermal or intradermal.

12. The method of claim 7, wherein the administration is by a botulinum toxin implant.

13. The method of claim 7, wherein administration of a botulinum toxin type A is no less than about 1 to about 200 units per administration site, per patient treatment session.

14. The method of claim 7, wherein administration of a botulinum toxin type B is no less than about 40 to about 2500 units per administration site, per patient treatment session.

15. A method for treating a keloid in a patient in need thereof, the method comprising the step of administering a dose of a botulinum toxin complex type A, to the keloid of the patient; wherein the dose administered is less than an amount used to paralyze a muscle, ranging between about $10^{-3}$ units/kg of patient weight and about 35 units/kg of patient weight, and which reduces the keloid in size by from about 20% to 100%.

16. The method of claim 15, wherein the administration is by injection directly to the keloid.

17. The method of claim 15, wherein the administration is by topical or subcutaneous administration of the botulinum toxin.

* * * * *

UNITED STATES PATENT AND TRADEMARK OFFICE
CERTIFICATE OF CORRECTION

PATENT NO. : 8,871,224 B2
APPLICATION NO. : 13/073741
DATED : October 28, 2014
INVENTOR(S) : Eric First Page 1 of 1

It is certified that error appears in the above-identified patent and that said Letters Patent is hereby corrected as shown below:

On the Title Page

Under "Related U.S. Application Data", item (63):
Change "Continuation-in-part of application No. 12/762,110, filed on Apr. 16, 2010, now Pat. No. 8,530,410, which is a continuation-in-part of application No. 10/731,973, filed on Dec. 9, 2003, now Pat. No. 8,048,423." to -- Continuation in part of U.S. Application No. 10/731,973, filed Dec. 9, 2003, now U.S. Patent No. 8,048,423, and a continuation in part of U.S. Application No. 12/762,110, filed Apr. 16, 2010, now U.S. Patent No. 8,530,410, which is a continuation application of U.S. Application No. 11/779,095, filed July 17, 2007, now abandoned, which is a continuation application of U.S. Application No. 10/817,036, filed Apr. 2, 2004, now abandoned. --

In the Specification

Column 1, Lines 7-10:
Change "This application is a continuation in part of U.S. application Ser. No. 10/731,973, filed Dec. 9, 2003, and U.S. application Ser. No. 12/762,110, filed Apr. 16, 2010, both incorporated entirely by reference." to -- This application is a continuation in part of U.S. Application No. 10/731,973, filed Dec. 9, 2003, now U.S. Patent No. 8,048,423. This application is also a continuation in part of U.S. Application No. 12/762,110, filed Apr. 16, 2010, now U.S. Patent No. 8,530,410, which is a continuation application of U.S. Application No. 11/779,095, filed July 17, 2007, now abandoned, which is a continuation application of U.S. Application No. 10/817,036, filed Apr. 2, 2004, now abandoned, each of which is incorporated entirely by reference. --

Signed and Sealed this
Seventh Day of November, 2017

Joseph Matal
*Performing the Functions and Duties of the
Under Secretary of Commerce for Intellectual Property and
Director of the United States Patent and Trademark Office*